United States Patent
Perez Blanco et al.

(10) Patent No.: US 7,677,110 B2
(45) Date of Patent: Mar. 16, 2010

(54) METHOD AND APPARATUS FOR MEASURING THE ELASTICITY OF MATERIALS FOR LINING VEHICLE COMPONENTS

(75) Inventors: María Monica Perez Blanco, Vigo (ES); Jorge Juan Blanco Fernandez, Vigo (ES); Francisco Fernández Pintelos, Vigo (ES)

(73) Assignee: Dalphi Metal Espana S.A., Madrid (ES)

( * ) Notice: Subject to any disclaimer, the term of this patent is extended or adjusted under 35 U.S.C. 154(b) by 69 days.

(21) Appl. No.: 12/142,410

(22) Filed: Jun. 19, 2008

(65) Prior Publication Data
US 2009/0000398 A1 Jan. 1, 2009

(30) Foreign Application Priority Data
Jun. 19, 2007 (EP) .................................. 07381046

(51) Int. Cl.
*G01L 1/04* (2006.01)
(52) U.S. Cl. ..................................... 73/826; 73/862.471
(58) Field of Classification Search ........... 73/760–860, 73/862.471
See application file for complete search history.

(56) References Cited
U.S. PATENT DOCUMENTS

| | | | | |
|---|---|---|---|---|
| 3,881,346 A | * | 5/1975 | Scheucher | 73/829 |
| 4,315,427 A | * | 2/1982 | Leiter et al. | 73/52 |
| 4,794,805 A | * | 1/1989 | Carney et al. | 73/862.452 |
| 5,287,756 A | * | 2/1994 | Tassic | 73/862.391 |
| 5,461,757 A | * | 10/1995 | Leifeld | 19/239 |
| 5,684,596 A | * | 11/1997 | Eslinger et al. | 356/614 |
| 6,006,608 A | * | 12/1999 | Renz et al. | 73/800 |
| 6,629,466 B2 | * | 10/2003 | Grote et al. | 73/857 |
| 7,047,156 B1 | * | 5/2006 | Bechtel et al. | 702/179 |

* cited by examiner

Primary Examiner—Max Noori
(74) Attorney, Agent, or Firm—Ladas & Parry LLP

(57) ABSTRACT

The invention relates to a non-destructive method for measuring the elasticity of templates of materials for lining automotive vehicle components, characterized in that it comprises the following steps: applying a tensile pre-load with a predetermined value P1 in a longitudinal direction to a template section (41); applying a tensile load with a predetermined value P2 in a longitudinal direction to said section (41) and measuring the longitudinal deformation produced; removing the load applied to said section (41) and measuring the residual longitudinal deformation produced. The invention also comprises an apparatus (11) for carrying out the method which comprises two fixing elements (15, 17) for fixing the section (41), one of which elements is a fixed element (15) and the other is a moving element (17), a device for applying a tensile load to the moving element (17) connected to a dynamometer (29), and a rule (31) for measuring the longitudinal deformation of said section (41).

7 Claims, 1 Drawing Sheet

METHOD AND APPARATUS FOR MEASURING THE ELASTICITY OF MATERIALS FOR LINING VEHICLE COMPONENTS

FIELD OF THE INVENTION

The present invention relates to a method and apparatus for measuring the elasticity of materials, and more particularly to an apparatus and a non-destructive method for measuring the elasticity of materials for lining steering wheels and other automotive vehicles.

BACKGROUND OF THE INVENTION

Tests in which a sample of the material is subjected to tension, typically until it breaks, are usually used to measure the elasticity of the materials.

In these tests, the sample is secured at its ends, a load is applied moving an actuator joined to an end of the sample, whereas the other end remains fixed and the load applied and the elongation of the sample are measured.

In the case of leather used to line vehicle steering wheels, the industry has standardized destructive tests such as that described in standard DIN 53 328.

Non-destructive tests are also known in the leather industry such as those described in patent applications EP 0866327 and EP 1081235, which are used to check different quality aspects of the parts in order to be able to provide the necessary guarantees to its recipients.

For the particular case of materials used to line certain vehicle components, particularly steering wheels, additional methods for measuring elasticity which allow improving the processes for lining said components are necessary.

The present invention is aimed at satisfying this need.

SUMMARY OF THE INVENTION

An objective of the present invention is to provide a method and apparatus for measuring the elasticity of a template of a material used to line automotive vehicle components which allow obtaining representative measurements of the real stretching of said material occurring during the lining process.

Another objective of the present invention is to provide a method and apparatus for measuring the elasticity of a template of a material used to line automotive vehicle components which do not require destroying the template.

Another objective of the present invention is to provide a method and apparatus for measuring the elasticity of a template of a material used to line automotive vehicle components which can be applied to the templates of material used during the process for lining said components.

In one aspect, these and other objectives are achieved by providing a non-destructive method for measuring the elasticity of templates of materials for lining automotive vehicles comprising the following steps.

applying a tensile pre-load with a predetermined value P1 in a longitudinal direction to a template section;

applying a tensile load with a predetermined value P2 in a longitudinal direction to said template section and measuring the longitudinal deformation produced;

removing the load applied to said template section and measuring the residual longitudinal deformation.

In another aspect, the mentioned objects are achieved by providing an apparatus for carrying out said method, comprising:

two fixing elements for fixing a template section, one of which elements is fixed and the other is moving;

a device for applying a tensile load to the moving element connected to a dynamometer;

a rule for measuring the longitudinal deformation of said template section.

In a preferred embodiment of the invention, said template is made of leather and is used to line automotive vehicle steering wheels.

Other features and advantages of the present invention will be understood from the following detailed description of an illustrative and by no means limiting embodiment of its object in relation to the attached drawings.

DETAILED DESCRIPTION OF THE INVENTION

Figure 1:
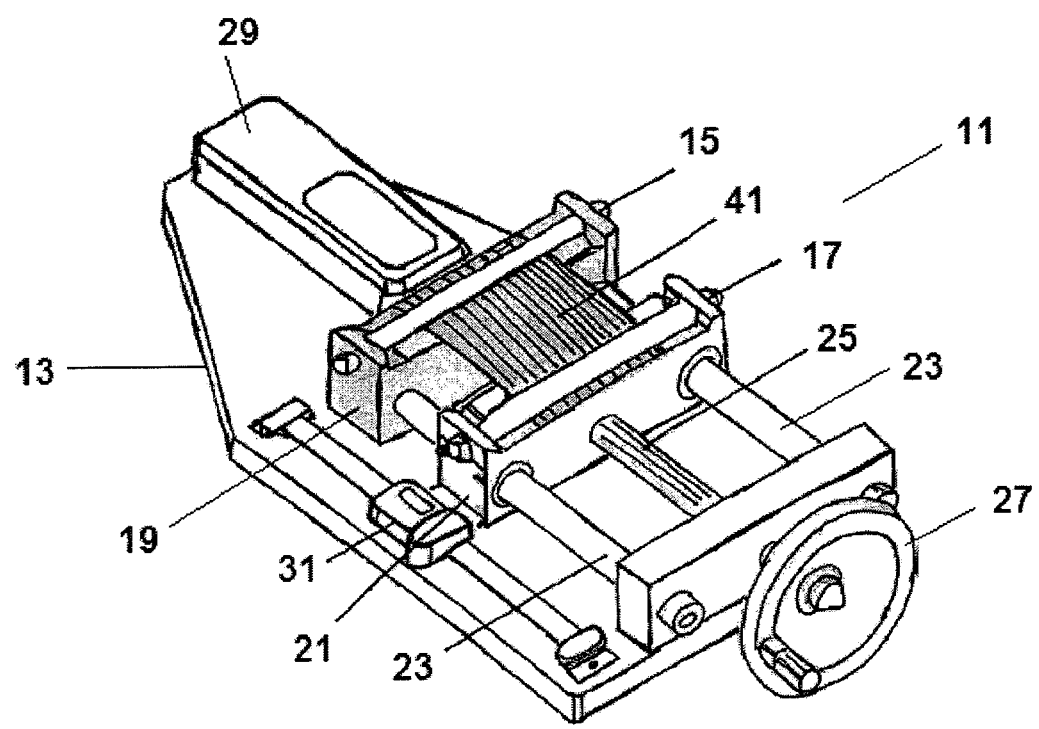
FIG. 1 shows a schematic perspective view of an apparatus for measuring the elasticity of a template of a material used to line automotive vehicle components according to the present invention.

According to FIG. 1, a preferred embodiment of an apparatus 11 for measuring the elasticity of a template of a material used to line automotive vehicle components is observed, comprising the following elements:

A base 13 supporting all the components of the apparatus.

Two fixing elements 15, 17 for fixing the transverse ends of the template section 41 object of the test.

A rigid support 19 of the fixing element 15.

A moving support 21 of the fixing element 17.

Guides 23 for moving the moving support 21.

A device for applying a longitudinal tensile load to the template section 41, formed by a drive spindle 25 connected to a tightening wheel 27.

A dynamometer 29 associated to the drive spindle 25 such that it can measure the load applied to the section 41 without the influence of the system friction.

A rule 31 to measure the longitudinal deformation of the section 41 when tensile loads are applied to it.

The dynamometer 29 and the rule 21 can include elements which allow digitally representing and/or transmitting the load and movement measurements made during the test.

For its part, in a preferred embodiment, the method for measuring the elasticity of templates of materials for lining automotive vehicle components according to the present invention comprises the following steps:

Arranging a template section 41 of material to be tested between the fixing elements 15, 17. In a preferred embodiment of the invention, the template section 41 would be a portion thereof with a minimum longitudinal dimension (in the tensile load application direction) of 100 mm and with the same transverse dimension as that of the template, which in any case can be considered to be comprised between 50 and 150 mm in the templates used for lining vehicle components in which the method of the present invention is especially interesting.

FIG. 1 only shows the template section 41 for the sake of simplicity but it must be understood that the entire template would be used in the test but only section 41 would be fixed to the apparatus.

Applying a tensile pre-load with a certain value P1 moving the drive spindle 25 with the tightening wheel 27 until it is supported in the dynamometer 29 and applies said pre-load (allowing the reading thereof in the dynamometer), which in a preferred embodiment is comprised between 5-6 Nw. In that position, the rule 31 for measuring the longitudinal measurement is placed in position 0.

Applying a tensile load with a predetermined value P2 by means of the corresponding movement of the drive spindle 25 with the tightening screw 27 and taking the measurement of the longitudinal displacement indicated by rule 31.

Removing the tensile load P2 by means of a movement of the drive spindle 25 in the opposite direction to that of the previous step, maintaining the pre-load P1, and taking the measurement of the residual displacement indicated by rule 31

Removing the template of material from the apparatus 11, which can be intended for lining a steering wheel or another vehicle component.

The values of longitudinal displacement and residual displacement obtained by means of the mentioned method, applying a predetermined load can respectively be determined as the absolute elasticity value (E1) and the plastic deformation value (E2) of the material in question. For its part, the result of the expression (E2/E1)×100 can be called elasticity percentage.

These parameters, referred to a certain number of tests, can be used to establish certain objective acceptance criteria of the material in question.

An advantage of the method object of the present invention, compared to the leather testing standard, tensile test DIN 53 328, relating to the measurement of elongation under tension, is the possibility of using the entire width of the template, which allows the ratio between the tensile load and the cross-section to be very low. This involves a greater accuracy in the measurement of the longitudinal displacement in the tensile load ranges required in the processes for lining steering wheels or other automotive wheel components.

Another advantage of the method object of the present invention is its non-destructive nature such that an elasticity value can be obtained which can later be verified in the lining process, in addition to the fact that the template is question can be used for manufacture.

Another advantage of the method object of the present invention is that the real elasticity is measured in conditions similar to those of the process for lining the component in question.

Another advantage of the method object of the present invention is that measurements can be made in different areas of the template without destroying it, which is useful when the template is assembled with several parts and especially if the materials of each of such parts are different.

Although several embodiments of the invention have been described and shown, it is evident that modifications comprised within the scope of the invention can be introduced therein, such invention must not be considered as limited to said embodiments but to the content of the following claims.

The invention claimed is:

1. A non-destructive method for measuring the elasticity of templates of materials for lining automotive vehicle components, characterized in that it comprises the following steps:
   a) applying a tensile pre-load with a predetermined value P1 in a longitudinal direction to a template section (41);
   b) applying a tensile load with a predetermined value P2 in a longitudinal direction to said template section (41) and measuring the longitudinal deformation produced;
   c) removing the load applied to said template section (41) and measuring the residual longitudinal deformation produced.

2. A non-destructive method for measuring the elasticity of templates of materials for lining automotive vehicle components according to claim 1, characterized in that said template section (41) has a minimum longitudinal dimension of 100 mm.

3. A non-destructive method for measuring the elasticity of templates of materials for lining automotive vehicle components according to claim 2, characterized in that the transverse dimension of the template is comprised between 50 and 150 mm.

4. A non-destructive method for measuring the elasticity of templates of materials for lining automotive vehicle components according to claim 1, characterized in that the vehicle component which is lined with said template is the steering wheel.

5. A non-destructive method for measuring the elasticity of templates of materials for lining automotive vehicle components according to claim 1, characterized in that the material of the template is leather.

6. An apparatus (11) for carrying out the method object of claim 1, characterized in that it comprises: two fixing elements (15, 17) for fixing a template section (41), one of which elements is a fixed element (15) and the other is a moving element (17), a device for applying a tensile load to the moving element (17) connected to a dynamometer (29), and a rule (31) for measuring the longitudinal deformation of said template section (41).

7. An apparatus (11) according to claim 6, characterized in that the device for applying a tensile load comprises a tightening wheel (27) connected to a drive spindle (25) of said moving fixing element (17).

* * * * *